(12) United States Patent
Fujiwara et al.

(10) Patent No.: US 8,546,633 B2
(45) Date of Patent: Oct. 1, 2013

(54) METHOD FOR PRODUCING ALKYLATED AROMATIC COMPOUND, METHOD FOR PRODUCING CUMENE, AND METHOD FOR PRODUCING PHENOL

(75) Inventors: Kenji Fujiwara, Kamakura (JP); Tsuneyuki Ohkubo, Ichihara (JP); Terunori Fujita, Yokohama (JP); Shinobu Aoki, Ichihara (JP); Masayasu Ishibashi, Ichihara (JP); Masao Imai, Yokohama (JP); Kozo Yasuda, Chiba (JP)

(73) Assignee: Mitsui Chemicals, Inc., Tokyo (JP)

( * ) Notice: Subject to any disclaimer, the term of this patent is extended or adjusted under 35 U.S.C. 154(b) by 272 days.

(21) Appl. No.: 13/125,163

(22) PCT Filed: Oct. 22, 2009

(86) PCT No.: PCT/JP2009/068168
§ 371 (c)(1),
(2), (4) Date: Apr. 20, 2011

(87) PCT Pub. No.: WO2010/047364
PCT Pub. Date: Apr. 29, 2010

(65) Prior Publication Data
US 2011/0201846 A1 Aug. 18, 2011

(30) Foreign Application Priority Data
Oct. 23, 2008 (JP) ................ 2008-273233

(51) Int. Cl.
*C07C 2/86* (2006.01)
*C07C 37/08* (2006.01)

(52) U.S. Cl.
USPC ........... 585/467; 585/446; 585/449; 585/450; 585/454; 585/469; 568/798

(58) Field of Classification Search
None
See application file for complete search history.

(56) References Cited

U.S. PATENT DOCUMENTS

| 5,015,786 | A | 5/1991 | Araki et al. |
|---|---|---|---|
| 5,017,729 | A | 5/1991 | Fukuhara et al. |
| 6,512,153 | B1 | 1/2003 | Cappellazzo et al. |
| 6,841,704 | B2 | 1/2005 | Sakuth et al. |
| 7,019,185 | B2 * | 3/2006 | Dandekar et al. ............ 585/467 |
| 7,524,788 | B2 | 4/2009 | Girotti et al. |
| 7,790,936 | B2 * | 9/2010 | Takai et al. ............ 568/715 |
| 2004/0162448 | A1 | 8/2004 | Yang et al. |
| 2005/0075239 | A1 * | 4/2005 | Girotti et al. ............ 502/64 |
| 2010/0022812 | A1 * | 1/2010 | Takai et al. ............ 585/467 |

FOREIGN PATENT DOCUMENTS

| FR | 1030020 | 9/1953 |
|---|---|---|
| JP | 57-091972 | 6/1982 |
| JP | 2-174737 | 7/1990 |
| JP | 2-231442 | 9/1990 |
| JP | 11-035497 | 2/1999 |
| JP | 2001-55351 | 2/2001 |
| JP | 2003-523985 | 8/2003 |
| JP | 2005-513116 | 5/2005 |
| WO | 2008/062644 | 5/2008 |

OTHER PUBLICATIONS

Database CAPLUS on STN, Acc. No. 2008:1042754, Takai et al., WO 2008102664 (Aug. 28, 2008) (abstract).*
International Search Report dated Feb. 2, 2010.

* cited by examiner

*Primary Examiner* — Brian J Davis
(74) *Attorney, Agent, or Firm* — Rankin, Hill & Clark LLP

(57) ABSTRACT

A method for producing an alkylated aromatic compound includes a step (i) of producing a reaction product (a1) containing the alkylated aromatic compound and water by the reaction of an aromatic compound, a ketone, and hydrogen using a metal component containing at least one metallic element of copper, nickel, cobalt, and rhenium and a solid acid substance; a step (ii) of forming a dehydrated product (a2) from at least a portion of the reaction product (a1) by removing at least a portion of the water in the reaction product (a1); and a step (iii) of producing a reaction product (a3) containing the alkylated aromatic compound by bringing at least a portion of the dehydrated product (a2) into contact with a solid acid substance.

17 Claims, 4 Drawing Sheets

US 8,546,633 B2

METHOD FOR PRODUCING ALKYLATED AROMATIC COMPOUND, METHOD FOR PRODUCING CUMENE, AND METHOD FOR PRODUCING PHENOL

TECHNICAL FIELD

The present invention relates to a method for producing an alkylated aromatic compound, a method for producing cumene, and a method for producing phenol.

BACKGROUND ART

A method for producing cumene by the reaction between benzene and propylene, a method for producing cumene hydroperoxide by the oxidation of cumene, and a method for producing phenol and acetone by the acidolysis of cumene hydroperoxide are known. A combined method of these reactions is a method for producing phenol generally referred to as the cumene process and is a mainstream method for producing phenol.

One of the characteristics of the cumene process is the production of acetone as a by-product. This is advantageous when acetone is desired. However, when acetone is surplus to requirements, an unfavorable price difference between acetone and the raw material propylene causes a serious drawback.

In order to improve the price relationship between the raw material olefin and a by-product ketone, for example, a method has been proposed in which the oxidation and acidolysis of secondary butylbenzene produced from n-butene and benzene yields phenol and methyl ethyl ketone (see, for example, Patent Literatures 1 and 2). However, the selectivity for the target secondary butylbenzene hydroperoxide in the oxidation of secondary butylbenzene in this method is only approximately 80%, and 15% or more acetophenone is produced as a by-product. Thus, this method for producing phenol has a smaller yield than the cumene process.

Another method has been proposed in which the oxidation and acidolysis of cyclohexylbenzene produced from cyclohexene and benzene yields phenol and cyclohexanone. This method involves the dehydrogenation of cyclohexanone into phenol, thereby formally avoiding the production of a by-product ketone. However, the method has a still lower yield in the oxidation reaction of cyclohexylbenzene into the target cyclohexylbenzene hydroperoxide. Thus, the method is of low industrial value (see, for example, Patent Literature 3).

Regarding the cumene process having the highest yield in the oxidation and acidolysis, in order to avoid the problem of the raw material propylene and the by-product acetone while securing the advantages of the cumene process, a method has been proposed in which the by-product acetone is used as a raw material for the cumene process by various methods.

Acetone can be easily hydrogenated to produce isopropanol. The dehydration reaction of isopropanol yields propylene, which is then reacted with benzene to yield cumene. Thus, the process proposed uses acetone as a raw material for the cumene process (see, for example, Patent Literature 4).

Still another method has been proposed in which isopropanol produced by the hydrogenation of acetone is directly reacted with benzene to produce cumene (see, for example, Patent Literature 5 and Patent Literature 6).

A process method has been proposed in which acetone is converted into isopropanol, isopropanol is reacted with benzene to produce cumene, and cumene is used to produce phenol (see, for example, Patent Literature 7).

Still another method has been proposed in which acetone is directly reacted with benzene in the presence of hydrogen (see, for example, Patent Literature 8).

The alkylation of benzene with isopropanol or via isopropanol in a reaction system produces water. Since water reduces the acid strength of an acid catalyst, which is an alkylation catalyst (see, for example, Patent Literature 9), the acid catalyst is required in large quantities. This is a great problem in commercialization.

CITATION LIST

Patent Literature

PTL 1: Japanese Unexamined Patent Application Publication No. S57-91972
PTL 2: U.S. Patent Application Publication No. 2004/0162448
PTL 3: France Patent No. 1030020
PTL 4: Japanese Unexamined Patent Application Publication No. H2-174737
PTL 5: Japanese Unexamined Patent Application Publication No. H2-231442
PTL 6: Japanese Unexamined Patent Application Publication No. H11-35497
PTL 7: Japanese Unexamined Patent Application Publication (Translation of PCT Application) No. 2003-523985
PTL 8: Japanese Unexamined Patent Application Publication (Translation of PCT Application) No. 2005-513116
PTL 9: Japanese Unexamined Patent Application Publication No. 2001-55351

SUMMARY OF INVENTION

Technical Problem

The following is an exemplary known method for producing cumene by the reaction of raw materials including benzene, acetone, and hydrogen. In this known method, cumene is produced by an exothermic reaction of raw materials including benzene, acetone, and hydrogen in an adiabatic reactor, which contains a solid acid substance and a metal component containing at least one metallic element selected from the group consisting of copper, nickel, cobalt, and rhenium. After reaction liquid and reaction gas containing cumene are collected from the adiabatic reactor, the reaction gas is cooled to separate liquid in the reaction gas, yielding a separated gas and a separated liquid. The oil-water separation of the reaction liquid yields an oil component from which at least a portion of water has been removed. In the known method, at least a portion of the separated gas and a portion of the oil component are generally returned to the adiabatic reactor as circulating gas and circulating liquid to remove heat of reaction. FIG. 1 illustrates the flow chart (process drawing) of the known method. In the known method, a mixture of the solid acid substance and the metal component is generally fed to the adiabatic reactor, or the metal component and the solid acid substance are fed to the upstream side and the downstream side, respectively.

The production of an alkylated aromatic compound, such as cumene, by the reaction of raw materials including an aromatic compound, such as benzene, a ketone, such as acetone, and hydrogen, is accompanied by the production of water. The water content increases as the reaction proceeds or the raw materials flow downstream in the adiabatic reactor. The activity of the solid acid substance generally decreases in the presence of water. When low activity of the solid acid substance results in the production of an alkylated aromatic compound, such as cumene, at an insufficient reaction rate in the reactor, the reaction gas may contain a reaction intermediate olefin, such as propylene. The olefin, such as propylene, returned as a circulating reaction gas into the adiabatic reactor reacts with hydrogen in the presence of the metal component to yield paraffin, such as propane. The paraffin, such as propane, is not involved in the production of an alkylated aromatic compound, such as cumene, and therefore has considerable economic disadvantages. In order to prevent the production of the olefin, such as propylene, it is desirable that the alkylated aromatic compound, such as cumene, is produced in the reactor at a sufficient reaction rate. However, when the solid acid substance has low activity because of water, the production of the alkylated aromatic compound, such as cumene, at a sufficient reaction rate requires the solid acid substance in large quantities.

It is an object of the present invention to provide a method for producing an alkylated aromatic compound by the direct reaction of a ketone, hydrogen, and an aromatic compound. This method for producing an alkylated aromatic compound can greatly reduce the amount of solid acid substance as compared with known methods for producing an alkylated aromatic compound. It is another object of the present invention to provide a method for producing cumene by the direct reaction of acetone, hydrogen, and benzene. This method for producing cumene can greatly reduce the amount of solid acid substance as compared with known methods for producing cumene. It is still another object of the present invention to provide a method for producing phenol including the step of producing cumene by the method described above.

Solution to Problem

As a result of diligent research to solve the problems described above, the present inventors completed the present invention by finding that the problems can be solved by producing a reaction product by the direct reaction of a ketone, hydrogen, and an aromatic compound using a metal component and a solid acid substance, removing water from the reaction product, and bringing the reaction product into contact with the solid acid substance again.

The present invention relates to the following (1) to (17).

(1) A method for producing an alkylated aromatic compound, including a step (i) of producing a reaction product (a1) containing the alkylated aromatic compound and water by the reaction of an aromatic compound, a ketone, and hydrogen using a metal component containing at least one metallic element selected from the group consisting of copper, nickel, cobalt, and rhenium and a solid acid substance; a step (ii) of forming a dehydrated product (a2) from at least a portion of the reaction product (a1) by removing at least a portion of the water in the reaction product (a1); and a step (iii) of producing a reaction product (a3) containing the alkylated aromatic compound by bringing at least a portion of the dehydrated product (a2) into contact with a solid acid substance.

(2) The method for producing an alkylated aromatic compound according to (1), wherein the water content of the reaction product (a1) ranges from 0.5% to 10% by weight.

(3) The method for producing an alkylated aromatic compound according to (1) or (2), wherein the step (ii) includes a step (ii-1) of forming a reaction gas and a reaction liquid by the gas-liquid separation of the reaction product (a1), a step (ii-2) of forming a separated gas and a separated liquid by cooling the reaction gas to separate liquid in the reaction gas, and a step (ii-3) of forming an oil component from which at least a portion of water has been removed by oil-water separation of the reaction liquid, wherein the separated gas and the oil component are used as at least a portion of the dehydrated product (a2).

(4) The method for producing an alkylated aromatic compound according to (3), wherein the step (ii-3) is a step of forming an oil component from which at least a portion of water has been removed by oil-water separation of the reaction liquid and the separated liquid formed in the step (ii-2).

(5) The method for producing an alkylated aromatic compound according to any one of (1) to (4), wherein the step (i) is performed in an adiabatic reactor.

(6) The method for producing an alkylated aromatic compound according to any one of (1) to (5), wherein the metal component further contains at least one element selected from the group consisting of group IIB elements, group IIIA elements, group VIB elements, and group VIII elements (except nickel and cobalt).

(7) The method for producing an alkylated aromatic compound according to any one of (1) to (6), wherein the solid acid substance is zeolite.

(8) A method for producing cumene, wherein the aromatic compound and the ketone in the method for producing an alkylated aromatic according to any one of (1) to (7) are benzene and acetone, respectively.

(9) A method for producing cumene, including a step (I) of supplying benzene, acetone, and hydrogen to an adiabatic reactor that includes, from the upstream side, a catalyst layer (A) containing a solid acid substance (1), a catalyst layer (B) containing a metal component containing at least one metallic element selected from the group consisting of copper, nickel, cobalt, and rhenium, and a catalyst layer (C) containing a solid acid substance (2), or an adiabatic reactor that includes, from the upstream side, the catalyst layer (A) containing the solid acid substance (1) and a catalyst layer (D) containing a metal component containing at least one metallic element selected from the group consisting of copper, nickel, cobalt, and rhenium and the solid acid substance (2) and collecting reaction liquid and reaction gas containing cumene from an outlet of the adiabatic reactor located downstream of the catalyst layer (C) or the catalyst layer (D); a step (II) of forming a separated gas and a separated liquid by cooling the reaction gas to separate liquid in the reaction gas; a step (III) of forming an oil component from which at least a portion of water has been removed by oil-water separation of the reaction liquid; and a step (IV) of supplying at least a portion of the separated gas and at least a portion of the oil component to the adiabatic reactor as circulating gas and circulating liquid.

(10) The method for producing cumene according to (9), further including a step (V) of collecting reaction liquid and reaction gas containing cumene from an outlet of the adiabatic reactor located downstream of the catalyst layer (A) and upstream of the catalyst layer (B) or the catalyst layer (D).

(11) A method for producing cumene, including a step (I') of supplying benzene, acetone, and hydrogen to an adiabatic reactor that includes, from the upstream side, a catalyst layer (B) containing a metal component containing at least one metallic element selected from the group consisting of copper, nickel, cobalt, and rhenium and a catalyst layer (C) containing a solid acid substance (2), or an adiabatic reactor that includes a catalyst layer (D) containing a metal component containing at least one metallic element selected from the group consisting of copper, nickel, cobalt, and rhenium and the solid acid substance (2) and collecting reaction liquid and reaction gas containing cumene from an outlet of the adiabatic reactor located downstream of the catalyst layer (C) or the catalyst layer (D); a step (II') of forming a separated gas and a separated liquid by cooling the reaction gas to separate liquid in the reaction gas; a step (III') of forming an oil component from which at least a portion of water has been removed by oil-water separation of the reaction liquid; and a step (IV') of supplying at least a portion of the separated gas and at least a portion of the oil component to an adiabatic reactor that includes a catalyst layer (A) containing a solid acid substance (1) and producing reaction liquid and reaction gas containing cumene.

(12) The method for producing cumene according to (11), further including a step (V') of forming a separated gas and a separated liquid by cooling the reaction gas produced in the step (IV') to separate liquid in the reaction gas; a step (VI') of forming an oil component from which at least a portion of water has been removed by oil-water separation of the reaction liquid produced in the step (IV'); and a step (VII') of supplying at least a portion of the separated gas and a portion of the oil component to the adiabatic reactor used in the step (I') as circulating gas and circulating liquid.

(13) The method for producing cumene according to any one of (9) to (12), wherein the metal component further contains at least one element selected from the group consisting of group IIB elements, group IIIA elements, group VIB elements, and group VIII elements (except nickel and cobalt).

(14) The method for producing cumene according to any one of (9) to (13), wherein at least one of the solid acid substance (1) and the solid acid substance (2) is zeolite.

(15) The method for producing cumene according to (14), wherein the zeolite is zeolite having a 10, 11, or 12-membered ring structure.

(16) The method for producing cumene according to (14), wherein the zeolite is at least one zeolite selected from the group consisting of beta zeolite and MCM-22.

(17) A method for producing phenol, including the following steps (a) to (e), wherein the step (c) is performed in accordance with a method for producing cumene according to any one of (8) to (16):

the step (a) of converting cumene into cumene hydroperoxide by oxidation;

the step (b) of converting cumene hydroperoxide into phenol and acetone by acidolysis;

the step (c) of synthesizing cumene by the reaction of benzene, acetone, and hydrogen using the acetone produced in the step (b);

the step (d) of purifying the cumene produced in the step (c); and the step (e) of supplying the cumene purified in the step (d) to the step (a).

Advantageous Effects of Invention

A method for producing an alkylated aromatic compound according to the present invention is a method for producing an alkylated aromatic compound by the direct reaction of a ketone, hydrogen, and an aromatic compound and can produce the alkylated aromatic compound with a less amount of solid acid substance than known methods. A method for producing cumene according to the present invention is a method for producing cumene by the direct reaction of acetone, hydrogen, and benzene and can produce cumene with a less amount of solid acid substance than known methods.

A method for producing phenol according to the present invention includes the method for producing cumene as one step and can use acetone produced as a by-product in the production of phenol. Thus, a method for producing phenol according to the present invention can produce phenol with process and economic advantages.

DESCRIPTION OF EMBODIMENTS

Figure 1:
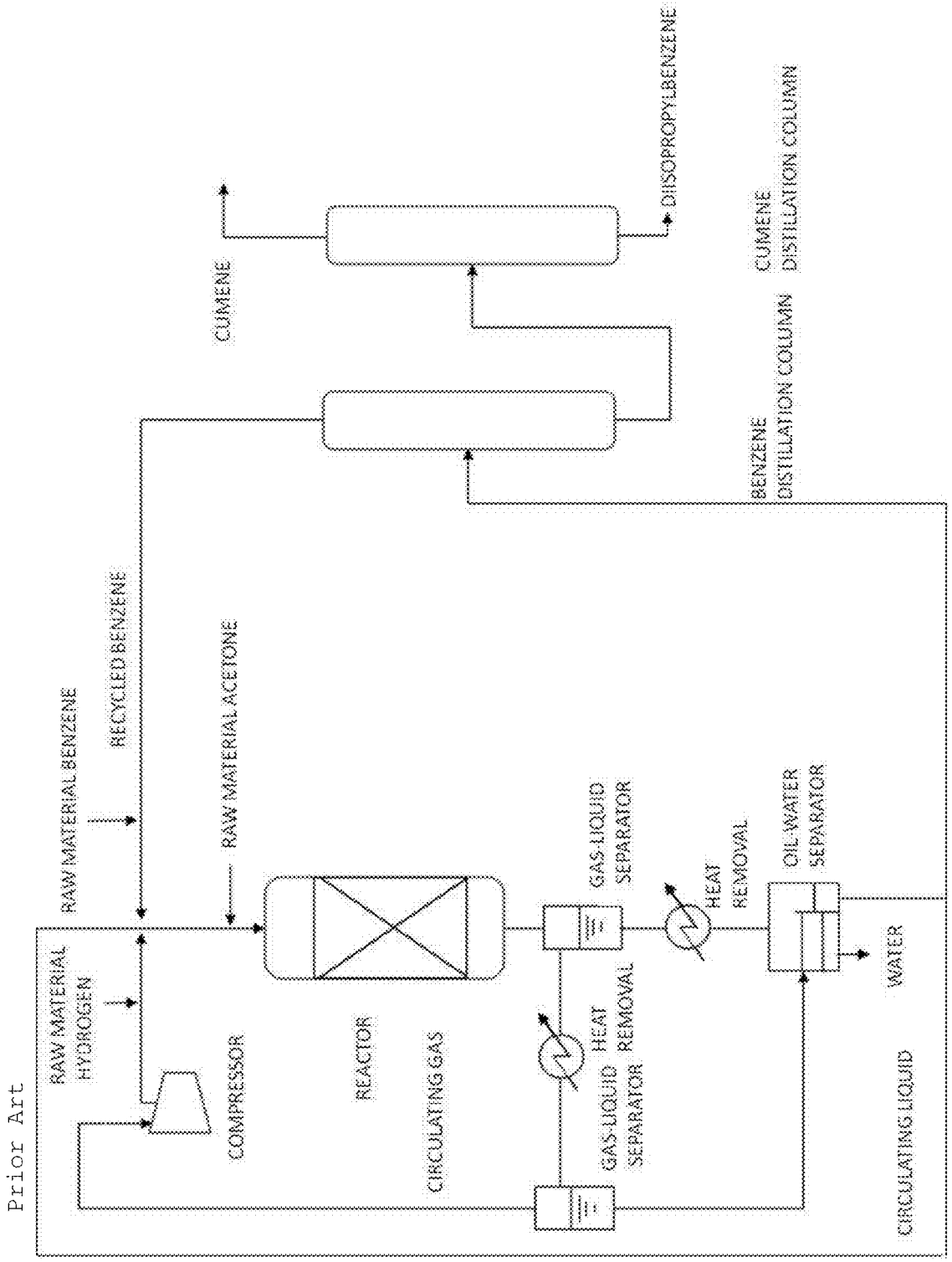
FIG. 1 is a flow chart of a known method for producing cumene from acetone, hydrogen, and benzene.

The present invention will now be more specifically described.

Method for Producing Alkylated Aromatic Compound

A method for producing an alkylated aromatic compound according to the present invention includes a step (i) of producing a reaction product (a1) containing the alkylated aromatic compound and water by the reaction of an aromatic compound, a ketone, and hydrogen using a metal component containing at least one metallic element selected from the group consisting of copper, nickel, cobalt, and rhenium and a solid acid substance; a step (ii) of forming a dehydrated product (a2) from at least a portion of the reaction product (a1) by removing at least a portion of the water in the reaction product (a1); and a step (iii) of producing a reaction product (a3) containing the alkylated aromatic compound by bringing at least a portion of the dehydrated product (a2) into contact with a solid acid substance.

A method for producing an alkylated aromatic compound according to the present invention includes a step of bringing a dehydrated product (a2) into contact with a solid acid substance. The dehydrated product (a2) is formed by removing at least a portion of the water in the reaction product (a1). This production method includes a step of removing at least a portion of water. Water is produced as a by-product during the production of an alkylated aromatic compound using a solid acid substance and reduces the activity of the solid acid substance. After this step, the reaction is performed again using a solid acid substance. Thus, the alkylated aromatic compound can be produced with sufficient reaction efficiency even with an amount of solid acid substance smaller than the amounts of solid acid substance used in known methods for producing an alkylated aromatic compound in which no dehydration is performed during the reaction.

Preferably, the water content of the reaction product (a1) ranges from 0.5% to 10% by weight.

The water content depends on the molar ratio of the aromatic compound to ketone, the percentage of the reaction product returned to the step (i), and other factors. When the aromatic compound in the step (i) is excessive, an excessive amount of the reaction product returned to the step (i) tends to result in a low water content. An excessive amount of the aromatic compound results in an increase in the cost of recovering the aromatic compound in purification and is an economic disadvantage. An excessive amount of the reaction product returned to the step (i) results in low productivity and is also an economic disadvantage. An excessively high water content unfavorably results in a marked decrease in the catalytic activity of the solid acid substance.

The step (ii) is a step of removing at least a portion of the water in the reaction product (a1) by dehydration treatment of at least a portion of the reaction product (a1) containing water produced in the step (i) to form the dehydrated product (a2). The dehydration treatment method may be, but is not limited to, the separation of water with an oil-water separator, the removal of water with an adsorbent, or removal with a water separation membrane.

Preferably, the step (ii) includes a step (ii-1) of forming a reaction gas and a reaction liquid by the gas-liquid separation of the reaction product (a1), a step (ii-2) of forming a separated gas and a separated liquid by cooling the reaction gas to separate liquid in the reaction gas, and a step (ii-3) of forming an oil component from which at least a portion of water has been removed by oil-water separation of the reaction liquid. The separated gas and the oil component formed in the steps (ii-1) to (ii-3) are used as at least a portion of the dehydrated product (a2).

Preferably, the step (ii-3) is a step of forming an oil component from which at least a portion of water has been removed by oil-water separation of the reaction liquid and the separated liquid formed in the step (ii-2). The oil-water separation of the reaction liquid together with the separated liquid is preferred because it allows an oil component contained in the separated liquid to be recovered.

The step (i) and the step (iii) are generally performed in a fixed-bed reactor. Examples of the fixed-bed reactor include adiabatic reactors and external heat exchanger type reactors. In particular, the step (i) is preferably performed in an adiabatic reactor. The step (iii) is also preferably performed in an adiabatic reactor.

Embodiments of the step (i) and the step (iii) are described below in which the step (i) and the step (iii) are performed in a single reactor or in different reactors.

When the step (i) and the step (iii) are performed in a single reactor, the reactor is preferably an adiabatic reactor. Examples of the adiabatic reactor include an adiabatic reactor that includes, from the upstream side, a catalyst layer (A) containing a solid acid substance (1), a catalyst layer (B) containing a metal component containing at least one metallic element selected from the group consisting of copper, nickel, cobalt, and rhenium, and a catalyst layer (C) containing a solid acid substance (2), and an adiabatic reactor that includes, from the upstream side, the catalyst layer (A) containing the solid acid substance (1) and a catalyst layer (D) containing a metal component containing at least one metallic element selected from the group consisting of copper, nickel, cobalt, and rhenium and the solid acid substance (2). The step (i) can be performed by supplying an aromatic compound, a ketone, and hydrogen to these adiabatic reactors. The step (iii) can be performed by returning at least a portion of the dehydrated product (a2) formed in the step (ii) to the adiabatic reactor.

When the step (i) and the step (iii) are performed in different reactors, both of the reactors used for the step (i) and the step (iii) are preferably adiabatic reactors. The reactor used for the step (i) may be an adiabatic reactor that includes, from the upstream side, a catalyst layer (B) containing a metal component containing at least one metallic element selected from the group consisting of copper, nickel, cobalt, and rhenium and a catalyst layer (C) containing a solid acid substance (2), or an adiabatic reactor that includes a catalyst layer (D) containing a metal component containing at least one metallic element selected from the group consisting of copper, nickel, cobalt, and rhenium and the solid acid substance (2). The step (i) can be performed by supplying an aromatic compound, a ketone, and hydrogen to these adiabatic reactors. The reactor used for the step (iii) may be an adiabatic reactor that includes a catalyst layer (A) containing a solid acid substance (1). The step (iii) can be performed by supplying at least a portion of the dehydrated product (a2) formed in the step (ii) to the adiabatic reactor.

In a method for producing an alkylated aromatic compound according to the present invention, the reaction temperatures in the production of the alkylated aromatic compound, that is, the temperatures at which the step (i) and the step (iii) are performed generally range from 100° C. to 300° C. More specifically, since the reaction in the present invention is an exothermic reaction, the reactor temperatures at which the steps are performed have a gradient.

For example, when the step (i) and the step (iii) are performed in a single adiabatic reactor as described above, preferably, the temperature of the adiabatic reactor in the vicinity of a reactor inlet located upstream of the catalyst layer (A) ranges from 100° C. to 160° C., and the temperature in the vicinity of a reactor outlet located downstream of the catalyst layer (C) or the catalyst layer (D) ranges from 120° C. to 300° C. (the temperature in the vicinity of the reactor outlet is higher than the temperature in the vicinity of the reactor inlet). Alternatively, when the step (i) and the step (iii) are performed in different adiabatic reactors as described above, preferably, the temperature of an adiabatic reactor used for the step (i) in the vicinity of a reactor inlet located upstream of the catalyst layer (B) or the catalyst layer (D) ranges from 100° C. to 160° C., and the temperature in the vicinity of a reactor outlet downstream of the catalyst layer (C) or the catalyst layer (D) ranges from 120° C. to 300° C. (the temperature in the vicinity of the reactor outlet is higher than the temperature in the vicinity of the reactor inlet). Furthermore, preferably, the temperature of an adiabatic reactor used for the step (iii) in the vicinity of a reactor inlet located upstream of the catalyst layer (A) ranges from 100° C. to 250° C., and the temperature in the vicinity of a reactor outlet downstream of the catalyst layer (A) ranges from 120° C. to 300° C. (the temperature in the vicinity of the reactor outlet is higher than the temperature in the vicinity of the reactor inlet).

The solid acid substance and the metal component containing at least one metallic element selected from the group consisting of copper, nickel, cobalt, and rhenium for use in a method for producing an alkylated aromatic compound according to the present invention are not particularly limited and may be those described below in "Method for Producing Cumene".

In the step (i) in a method for producing an alkylated aromatic compound according to the present invention, it is assumed that a ketone is reduced by hydrogen into a corresponding alcohol (for example, isopropanol in the case that the ketone is acetone) by the action of the metal component containing at least one metallic element selected from the group consisting of copper, nickel, cobalt, and rhenium, and this is followed by an alkylation reaction between the corresponding alcohol and an aromatic compound by the action of the solid acid substance. It is also assumed that an alkylation reaction occurs between the aromatic compound and an olefin or ether produced by the intramolecular or intermolecular dehydration of a portion of the corresponding alcohol.

A method for producing an alkylated aromatic compound according to the present invention employs hydrogen as a raw material, as described above. The amount of hydrogen used may theoretically be at least equimolar to the amount of ketone. Considering separation and recovery, the amount of hydrogen is generally 1 to 10 times, preferably 1 to 5 times, the moles of ketone. The amount of hydrogen used may be smaller than the moles of ketone to reduce the conversion of the ketone to 100% or less.

Hydrogen supplied in the reaction according to the present invention reacts with an oxygen atom of a ketone to form a corresponding alcohol. This alcohol reacts with an aromatic compound to yield an alkylated aromatic compound and water. The reaction described above consumes hydrogen in an amount equimolar to the amount of the ketone. In the absence of undesirable side reactions, basically, the reaction does not consume extra hydrogen.

The amount of aromatic compound may theoretically be at least equimolar to the amount of ketone. Considering separation and recovery, the amount of aromatic compound is generally 1 to 10 times, preferably 1 to 5 times, the moles of ketone.

In the present invention, the aromatic compound may be a compound having 6 to 20 carbon atoms, for example, a benzene homolog, such as benzene, toluene, or xylene, a substituent derivative thereof, a naphthalene homolog, such as naphthalene or methylnaphthalene, or a substituent derivative thereof. The ketone may be a compound having 3 to 20 carbon atoms, an objective or a non-objective. Examples of a group bonded to the carbonyl group include alkyl groups and aryl groups. Specific examples include acetone, methyl ethyl ketone, and acetophenone.

Preferably, the aromatic compound is benzene, and the ketone is acetone. In this case, the alkylated aromatic compound produced is cumene. Thus, a method for producing an alkylated aromatic compound according to the present invention is preferably a method for producing cumene.

Specific embodiments of a method for producing an alkylated aromatic compound according to the present invention are embodiments in which benzene, acetone, and cumene in "Method for Producing Cumene" described below are replaced with an aromatic compound, a ketone, and an alkylated aromatic compound, respectively. The manufacturing conditions, such as the pressure, WHSV, and the amount of catalyst, may be the same as conditions described below in "Method for Producing Cumene". When a ketone other than acetone is used, reaction intermediates, such as propylene and isopropanol, described below in "Method for Producing Cumene" are reaction intermediates corresponding to the ketone.

Method for Producing Cumene

A method for producing cumene according to the present invention roughly includes a first embodiment and a second embodiment.

A method for producing cumene according to the present invention (the first embodiment) includes a step (I) of supplying benzene, acetone, and hydrogen to an adiabatic reactor that includes, from the upstream side, a catalyst layer (A) containing a solid acid substance (1), a catalyst layer (B) containing a metal component containing at least one metallic element selected from the group consisting of copper, nickel, cobalt, and rhenium, and a catalyst layer (C) containing a solid acid substance (2), or an adiabatic reactor that includes, from the upstream side, the catalyst layer (A) containing the solid acid substance (1) and a catalyst layer (D) containing a metal component containing at least one metallic element selected from the group consisting of copper, nickel, cobalt, and rhenium and the solid acid substance (2) and collecting reaction liquid and reaction gas containing cumene from an outlet of the adiabatic reactor located downstream of the catalyst layer (C) or the catalyst layer (D); a step (II) of forming a separated gas and a separated liquid by cooling the reaction gas to separate liquid in the reaction gas; a step (III) of forming an oil component from which at least a portion of water has been removed by oil-water separation of the reaction liquid; and a step (IV) of supplying at least a portion of the separated gas and at least a portion of the oil component to the adiabatic reactor as circulating gas and circulating liquid.

The method for producing cumene according to the present invention (the first embodiment) may further include a step (V) of collecting reaction liquid and reaction gas containing cumene from an outlet of the adiabatic reactor located downstream of the catalyst layer (A) and upstream of the catalyst layer (B) or the catalyst layer (D).

The method for producing cumene according to the present invention (the second embodiment) includes a step (I') of supplying benzene, acetone, and hydrogen to an adiabatic reactor that includes, from the upstream side, a catalyst layer (B) containing a metal component containing at least one metallic element selected from the group consisting of copper, nickel, cobalt, and rhenium and a catalyst layer (C) containing a solid acid substance (2), or an adiabatic reactor that includes a catalyst layer (D) containing a metal component containing at least one metallic element selected from the group consisting of copper, nickel, cobalt, and rhenium and the solid acid substance (2) and collecting reaction liquid and reaction gas containing cumene from an outlet of the adiabatic reactor located downstream of the catalyst layer (C) or the catalyst layer (D); a step (II') of forming a separated gas and a separated liquid by cooling the reaction gas to separate liquid in the reaction gas; a step (III') of forming an oil component from which at least a portion of water has been removed by oil-water separation of the reaction liquid; and a step (IV') of supplying at least a portion of the separated gas and at least a portion of the oil component to an adiabatic reactor that includes a catalyst layer (A) containing a solid acid substance (1) and producing reaction liquid and reaction gas containing cumene.

The method for producing cumene according to the present invention (the second embodiment) may further include a step (V') of forming a separated gas and a separated liquid by cooling the reaction gas produced in the step (IV') to separate liquid in the reaction gas; a step (VI') of forming an oil component from which at least a portion of water has been removed by oil-water separation of the reaction liquid produced in the step (IV'); and a step (VII') of supplying at least a portion of the separated gas and a portion of the oil component to the adiabatic reactor used in the step (I') as circulating gas and circulating liquid.

The method for producing cumene according to the present invention (the first embodiment) is characterized in that the catalyst layer (A) containing a solid acid substance (1) is disposed on the upstream side of the adiabatic reactor. The upstream side of the adiabatic reactor has a lower water concentration than the downstream side. Thus, even with a smaller amount of solid acid substance used in the production of cumene than in an embodiment in which a solid acid substance is disposed only on the downstream side of a reactor or an embodiment in which a mixture of a solid acid substance and a metal component is disposed in an adiabatic reactor as in known methods for producing cumene, reaction intermediates of the raw materials, such as isopropyl alcohol and propylene, can be allowed to appropriately react with benzene, thus yielding cumene at a sufficient reaction rate.

In a method for producing cumene according to the present invention (the second embodiment), an oil component is formed in the steps (the steps (II') and (III')) between the step (I') and the step (IV') by the removal of at least a portion of water from the reaction liquid produced in the step (I'), and the oil component is used in the step (IV'). Thus, the method for producing cumene according to the present invention (the second embodiment) includes the step of removing water between the steps using a solid acid substance (the steps (I') and (IV')). Even with a smaller amount of solid acid substance used in the production of cumene by the method for producing cumene according to the present invention (the second embodiment) than methods not including the step of removing water, the step of removing water that can reduce the activity of the solid acid substance allows reaction intermediates of the raw materials, such as isopropyl alcohol and propylene, to appropriately react with benzene, yielding cumene at a sufficient reaction rate.

In a method for producing cumene according to the present invention, the reaction temperature in the production of cumene, that is, the temperature of an adiabatic reactor generally ranges from 100° C. to 300° C. More specifically, since the reaction in the present invention is an exothermic reaction, the adiabatic reactor has a temperature gradient. In the method for producing cumene (the first embodiment), preferably, the temperature of the adiabatic reactor in the vicinity of a reactor inlet located upstream of the catalyst layer (A) ranges from 100° C. to 160° C., and the temperature in the vicinity of a reactor outlet located downstream of the catalyst layer (C) or the catalyst layer (D) ranges from 120° C. to 300° C. (the temperature in the vicinity of the reactor outlet is higher than the temperature in the vicinity of the reactor inlet). In the method for producing cumene (the second embodiment), preferably, the temperature of an adiabatic reactor used for the step (I') in the vicinity of a reactor inlet located upstream of the catalyst layer (B) or the catalyst layer (D) ranges from 100° C. to 160° C., and the temperature in the vicinity of a reactor outlet downstream of the catalyst layer (C) or the catalyst layer (D) ranges from 120° C. to 300° C. (the temperature in the vicinity of the reactor outlet is higher than the temperature in the vicinity of the reactor inlet). Furthermore, preferably, the temperature of an adiabatic reactor used for the step (IV') in the vicinity of a reactor inlet located upstream of the catalyst layer (A) ranges from 100° C. to 250° C., and the temperature in the vicinity of a reactor outlet downstream of the catalyst layer (A) ranges from 120° C. to 300° C. (the temperature in the vicinity of the reactor outlet is higher than the temperature in the vicinity of the reactor inlet).

In the present invention, the solid acid substance (1), the solid acid substance (2), and the metal component containing at least one metallic element selected from the group consisting of copper, nickel, cobalt, and rhenium are used as catalysts. Another component may also be used as a catalyst.

The solid acid substance (1) and the solid acid substance (2) for use in the present invention may be the same solid acid substance or different solid acid substances, preferably the same solid acid substance.

The solid acid substance (1) and the solid acid substance (2) for use in the present invention are catalysts having a function of an acid and may be generally referred to as solid acids. For example, zeolite, silica alumina, alumina, zirconia supported sulfate ions, and zirconia supported WO3 may be used.

In particular, zeolite, which is an inorganic crystalline porous compound containing silicon and aluminum, is a solid acid substance suitable for the present invention in terms of heat resistance and the target selectivity for cumene. These solid acid substances may be used alone or in combination.

Zeolite preferably has pores having approximately the same size as the molecular size of cumene and has a 10, 11, or 12-membered ring structure, more preferably a 12-membered ring structure.

Examples of zeolite having a 12-membered ring structure include a Y type, a USY type, a mordenite type, a dealuminated mordenite type, a β type, an MCM-22 type, and an MCM-56 type. Among these, beta zeolite, the MCM-22 type, and the MCM-56 type are suitable structures. In particular, beta zeolite and MCM-22 are preferred.

The ratio of silicon to aluminum in these zeolites may range from 2/1 to 200/1 and, in terms of activity and thermal stability, preferably 5/1 to 100/1. Isomorphously replaced zeolite may also be used in which aluminum atoms in the zeolite skeleton are substituted with a metal other than aluminum, such as Ga, Ti, Fe, Mn, or B.

The shape of the solid acid substance is not particularly limited and may be spherical, cylindrical, an extruded shape, or a crushed shape. The particle size of the solid acid substance may range from 0.01 to 100 mm depending on the reactor size.

The present invention employs a metal component containing at least one metallic element selected from the group consisting of copper, nickel, cobalt, and rhenium. The metal component may be simple substance of the metallic element, metal oxide, such as $ReO_2$, $Re_2O_7$, NiO, or CuO, metal chloride, such as $ReCl_3$, $NiCl_2$, or $CuCl_2$, or cluster metal, such as Ni—Cu or Ni—Cu—Cr. These metal components may be used alone or in combination.

The metal component containing at least one metallic element selected from the group consisting of copper, nickel, cobalt, and rhenium may be any metal component that can hydrogenate a carbonyl group into alcohol. Metal components commercially available as hydrogenation catalysts can be directly used. Metal components supported by various carriers are commercially available and may be used, for example, 5% Re carbon catalysts, 5% Re alumina catalysts, silica alumina supported nickel catalysts, and these catalysts with different loadings, such as 1% or 0.5%. Preferably, the carrier is at least one selected from the group consisting of silica, alumina, silica alumina, titania, magnesia, silica magnesia, zirconia, and carbon.

The shape of the metal component containing at least one metallic element selected from the group consisting of copper, nickel, cobalt, and rhenium is not particularly limited and may be spherical, cylindrical, an extruded shape, or a crushed shape. The particle size of the metal component may range from 0.01 to 100 mm depending on the reactor size.

The metal component containing at least one metallic element selected from the group consisting of copper, nickel, cobalt, and rhenium may further contain at least one element selected from the group consisting of group IIB elements, group IIIA elements, group VIB elements, and group VIII elements (except nickel and cobalt).

More specifically, the element is Zn, Cd, Hg, B, Al, Ga, In, Tl, Cr, Mo, W, Fe, Ru, Os, Rh, Ir, Pd, or Pt.

Among these, a metal component containing copper and Zn or Al is suitable to improve catalyst life.

A catalyst for use in the present invention may be another component. The addition of a metal salt, such as $PbSO_4$, $FeCl_2$, or $SnCl_2$, an alkali metal, such as K or Na, an alkali metal salt, or $BaSO_4$ as another component may improve activity or selectivity. Thus, another component may be added if necessary.

As described above, the catalyst layer (D) contains a metal component containing at least one metallic element selected from the group consisting of copper, nickel, cobalt, and rhenium and the solid acid substance (2).

A method (preparation method) for producing a catalyst containing the metal component containing at least one metallic element selected from the group consisting of copper, nickel, cobalt, and rhenium and the solid acid substance (2) forming the catalyst layer (D) is not particularly limited and may employ a catalyst produced by a physical mixture of the solid acid substance (2) and the metal component containing at least one metallic element selected from the group consisting of copper, nickel, cobalt, and rhenium at a catalyst particle level in the order of centimeters, or a catalyst produced by pulverizing the solid acid substance (2) and the metal component containing at least one metallic element selected from the group consisting of copper, nickel, cobalt, and rhenium, mixing them, and molding catalyst particles in the order of centimeters. The catalyst may be the metal component containing at least one metallic element selected from the group consisting of copper, nickel, cobalt, and rhenium supported by the solid acid substance (2) as a carrier, or the solid acid substance (2) supported by the metal component containing at least one metallic element selected from the group consisting of copper, nickel, cobalt, and rhenium as a carrier.

As described above, the catalyst constituting the catalyst layer (D) contains a metal component containing at least one metallic element selected from the group consisting of copper, nickel, cobalt, and rhenium and the solid acid substance (2). This catalyst can be produced by loading the solid acid substance (2) serving as a carrier with the metal component containing at least one metallic element selected from the group consisting of copper, nickel, cobalt, and rhenium, as described above. More specifically, the solid acid substance (2) may be loaded with the metal component by a method of impregnating the solid acid substance (2) with a nitrate aqueous solution of the metallic element and then firing the solid acid substance (2), a method of forming a complex of the metallic element and an organic molecule ligand to make the metallic element soluble in an organic solvent, dissolving the complex in the organic solvent, impregnating the solid acid substance (2) with the organic solvent, and firing the solid acid substance (2), or a vapor deposition method in the case that the complex can be vaporized under vacuum. A coprecipitation method of simultaneously performing the synthesis of the solid acid substance (2) and metal loading may also be employed in which the solid acid substance (2) is produced from a corresponding metal salt in the presence of a metal salt which will serve as a hydrogenation catalyst.

In a production method according to the present invention, it is assumed that acetone is reduced by hydrogen into isopropanol by the action of the metal component containing at least one metallic element selected from the group consisting of copper, nickel, cobalt, and rhenium in the catalyst layer (B) or the catalyst layer (D), and then the alkylation reaction between isopropanol and benzene occurs by the action of the solid acid substance (1) and the solid acid substance (2). It is also assumed that an alkylation reaction occurs between benzene and propylene or diisopropyl ether produced by the intramolecular or intermolecular dehydration of a portion of isopropanol.

In the method for producing cumene according to the present invention (the first embodiment), cumene is produced also in the catalyst layer (A) located upstream of the catalyst layer (B) or the catalyst layer (D) in which isopropanol is produced. This is because the circulating gas or the circulating liquid contains propylene, isopropanol, or diisopropyl ether in a production method according to the present invention, and an alkylation reaction between these compounds and benzene yields cumene.

In the method for producing cumene according to the present invention (the first embodiment), embodiments of catalyst layers disposed in the adiabatic reactor include an embodiment in which the following three layers are disposed from the upstream side: a catalyst layer (A) containing a solid acid substance (1), a catalyst layer (B) containing a metal component containing at least one metallic element selected from the group consisting of copper, nickel, cobalt, and rhenium, and a catalyst layer (C) containing a solid acid substance (2), and an embodiment in which the following two layers are disposed from the upstream side: the catalyst layer (A) containing the solid acid substance (1) and a catalyst layer (D) containing a metal component containing at least one metallic element selected from the group consisting of copper, nickel, cobalt, and rhenium and the solid acid substance (2).

Sequential charging of catalyst species suitable for each step of the reaction is a preferred charging method in terms of efficient use of the catalysts and the prevention of undesirable side reactions.

In the method for producing cumene according to the present invention (the first embodiment), therefore, a preferred one of the two embodiments described above is the embodiment in which the following three layers are disposed from the upstream side: a catalyst layer (A) containing a solid acid substance (1), a catalyst layer (B) containing a metal component containing at least one metallic element selected from the group consisting of copper, nickel, cobalt, and rhenium, and a catalyst layer (C) containing a solid acid substance (2).

In the method for producing cumene according to the present invention (the second embodiment), embodiments of catalyst layers disposed in the adiabatic reactor used for the step (I') include an embodiment in which the following two layers are disposed from the upstream side: a catalyst layer (B) containing a metal component containing at least one metallic element selected from the group consisting of copper, nickel, cobalt, and rhenium and a catalyst layer (C) containing a solid acid substance (2), and an embodiment in which the following one layer is disposed: a catalyst layer (D) containing a metal component containing at least one metallic element selected from the group consisting of copper, nickel, cobalt, and rhenium and the solid acid substance (2). A preferred one of these embodiments is the embodiment in which the following two layers are disposed from the upstream side: a catalyst layer (B) containing a metal component containing at least one metallic element selected from the group consisting of copper, nickel, cobalt, and rhenium and a catalyst layer (C) containing a solid acid substance (2).

A method for producing cumene according to the present invention employs hydrogen as a raw material, as described above.

The amount of hydrogen used may theoretically be at least equimolar to the amount of acetone. Considering separation and recovery, the amount of hydrogen is generally 1 to 10 times, preferably 1 to 5 times, the moles of acetone. The amount of hydrogen used may be smaller than the moles of acetone to reduce the conversion of the acetone to 100% or less.

Hydrogen supplied in the reaction according to the present invention reacts with an oxygen atom of acetone to form isopropyl alcohol. The isopropyl alcohol reacts with benzene to yield cumene and water. The reaction described above consumes hydrogen in an amount equimolar to the amount of acetone. In the absence of undesirable side reactions, basically, the reaction does not consume extra hydrogen.

The amount of benzene may theoretically be at least equimolar to the amount of acetone. Considering separation and recovery, the amount of benzene is generally 1 to 10 times, preferably 1 to 5 times, the moles of acetone.

In a method for producing cumene according to the present invention, the raw materials including benzene, acetone, and hydrogen are allowed to react, as described above.

In the method for producing cumene according to the present invention (the first embodiment), the position at which benzene is introduced into the adiabatic reactor is generally located upstream of the catalyst layer (A). In the method for producing cumene according to the present invention (the first embodiment), the position at which acetone is introduced into the adiabatic reactor may be located upstream of the catalyst layer (A), between the catalyst layer (A) and the catalyst layer (B), or between the catalyst layer (A) and the catalyst layer (D). In the method for producing cumene according to the present invention (the first embodiment), the position at which hydrogen is introduced into the adiabatic reactor may be located upstream of the catalyst layer (A), between the catalyst layer (A) and the catalyst layer (B), or between the catalyst layer (A) and the catalyst layer (D).

In the method for producing cumene according to the present invention (the second embodiment), the position at which benzene is introduced into the adiabatic reactor for the step (I') is generally located upstream of the catalyst layer (B) or the catalyst layer (D). In the method for producing cumene according to the present invention (the second embodiment), the position at which acetone is introduced into the adiabatic reactor for the step (I') is also generally located upstream of the catalyst layer (B) or the catalyst layer (D). In the method for producing cumene according to the present invention (the second embodiment), the position at which hydrogen is introduced into the adiabatic reactor for the step (I') is also generally located upstream of the catalyst layer (B) or the catalyst layer (D).

Benzene and acetone are introduced into the adiabatic reactor from the upstream side to the downstream side. Hydrogen may be introduced into the adiabatic reactor from the upstream side to the downstream side or from the downstream side to the upstream side.

In a method for producing cumene according to the present invention, therefore, a mixture containing acetone and benzene comes into contact with hydrogen in a gas-liquid countercurrent flow or a gas-liquid cocurrent flow. The flow direction of liquid and gas may be liquid downward-gas upward, liquid upward-gas downward, liquid and gas upward, or liquid and gas downward.

Hydrogen gas is generally continuously supplied to the adiabatic reactor but may be supplied otherwise. For example, hydrogen gas may be supplied intermittently, that is, hydrogen gas is supplied at the beginning of the reaction, then stopped, and supplied again after a predetermined period of time. For a liquid phase reaction, hydrogen gas dissolved in a solvent may be supplied. In a recycling process, hydrogen gas recovered from the top of the reactor together with a low-boiling fraction may be supplied. The pressure of hydrogen supplied is generally the same as the reactor pressure and may be appropriately altered in accordance with the method of supplying hydrogen.

The pressure in a method for producing cumene according to the present invention preferably ranges from 0.1 to 100 atm, more preferably 0.5 to 50 atm. More specifically, in a method for producing cumene according to the present invention, the step (I) is preferably performed in this pressure range in the first embodiment, and the steps (I') and (IV') are preferably performed in the pressure range in the second embodiment.

In the implementation of the present invention, the amount of catalyst used is not particularly limited. For example, in the reaction with a fixed-bed flow apparatus, the amount (weight) of all the raw materials (benzene, acetone, hydrogen, circulating liquid, and circulating gas) supplied per hour divided by the weight of catalysts, that is, WHSV desirably ranges from 0.1 to 200/h, more preferably 0.2 to 100/h. The weight of catalysts is the total amount of catalysts used in a method for producing cumene according to the present invention, that is, the total amount of the solid acid substance (1), the solid acid substance (2), and the metal component containing at least one metallic element selected from the group consisting of copper, nickel, cobalt, and rhenium. The amount (weight) of all the raw materials (benzene, acetone, hydrogen, circulating liquid, and circulating gas) supplied per hour divided by the weight of the solid acid catalysts, that is, WHSV (solid acid substances) desirably ranges from 0.2 to 400/h, more preferably 0.4 to 200/h.

In the method for producing cumene according to the present invention (the first embodiment), in the case that the catalyst layers in the adiabatic reactor according to an embodiment include the following three layers from the upstream side: a catalyst layer (A) containing a solid acid substance (1), a catalyst layer (B) containing a metal component containing at least one metallic element selected from the group consisting of copper, nickel, cobalt, and rhenium, and a catalyst layer (C) containing a solid acid substance (2), when the weight of the catalyst layer (A) is 100 parts by weight, the weight of the catalyst layer (B) preferably ranges from 10 to 1000 parts by weight, more preferably 50 to 500 parts by weight, and the weight of the catalyst layer (C) preferably ranges from 20 to 2000 parts by weight, more preferably 100 to 1000 parts by weight.

In the method for producing cumene according to the present invention (the first embodiment), in the case that the catalyst layers in the adiabatic reactor according to an embodiment include the following two layers from the upstream side: the catalyst layer (A) containing a solid acid substance (1) and a catalyst layer (D) containing a metal component containing at least one metallic element selected from the group consisting of copper, nickel, cobalt, and rhenium and a solid acid substance (2), when the weight of the catalyst layer (A) is 100 parts by weight, the weight of the catalyst layer (D) preferably ranges from 10 to 2000 parts by weight, more preferably 50 to 1000 parts by weight. When the total of the metal component containing at least one metallic element selected from the group consisting of copper, nickel, cobalt, and rhenium and the solid acid substance (2) is 100% by weight, the catalyst layer (D) preferably contains 5% to 45% by weight of the metal component and 55% to 95% by weight of the solid acid substance (2) and more preferably contains 10% to 40% by weight of the metal component and 60% to 90% by weight of the solid acid substance (2).

In the method for producing cumene according to the present invention (the second embodiment), in the case that the catalysts in an adiabatic reactor for the step (I') according to an embodiment include the following two layers from the upstream side: a catalyst layer (B) containing a metal component containing at least one metallic element selected from the group consisting of copper, nickel, cobalt, and rhenium and a catalyst layer (C) containing a solid acid substance (2), when the weight of the catalyst layer (B) is 100 parts by weight, the weight of the catalyst layer (C) preferably ranges from 10 to 1000 parts by weight, more preferably 20 to 500 parts by weight, and the weight of a catalyst layer (A) in an adiabatic reactor for the step (IV') preferably ranges from 20 to 2000 parts by weight, more preferably 100 to 1000 parts by weight.

In the method for producing cumene according to the present invention (the second embodiment), in the case that the catalyst in an adiabatic reactor for the step (I') according to an embodiment includes the following one layer: a catalyst layer (D) containing a metal component containing at least one metallic element selected from the group consisting of copper, nickel, cobalt, and rhenium and a solid acid substance (2), when the weight of the catalyst layer (D) is 100 parts by weight, the weight of a catalyst layer (A) in an adiabatic reactor for the step (IV') preferably ranges from 10 to 1000 parts by weight, more preferably 20 to 500 parts by weight. When the total of the metal component containing at least one metallic element selected from the group consisting of copper, nickel, cobalt, and rhenium and the solid acid substance (2) is 100% by weight, the catalyst layer (D) preferably contains 5% to 45% by weight of the metal component and 55% to 95% by weight of the solid acid substance (2) and more preferably contains 10% to 40% by weight of the metal component and 60% to 90% by weight of the solid acid substance (2).

The present invention is implemented by a continuous flow method. The present invention can be implemented in any of a liquid phase, a gas phase, and a gas-liquid mixed phase. A method for charging catalysts may be a fixed bed or a plate fixed bed, either of which may be used.

When the catalytic activity decreases after a certain elapsed time, the catalyst can be reactivated by a known regeneration method.

In order to ensure the production of a certain amount of cumene, a merry-go-round system may be employed in which two or three reactors are arranged in juxtaposition, and during the regeneration of one reactor the reaction is performed in the other one or two reactors. In the case of three reactors, the other two reactors may be connected in series to reduce fluctuations in the amount of production. With a fluidized-bed flow reaction system or a moving-bed reaction system, part or the entirety of the catalysts may be continuously or intermittently removed from the reactor while replenishing the reactor with the corresponding amount of catalysts to maintain the activity at a certain level.

The method for producing cumene according to the present invention (the first embodiment) produces cumene by the reaction of the raw materials including benzene, acetone, and hydrogen in the adiabatic reactor. Reaction liquid and reaction gas containing cumene are removed from an outlet of the adiabatic reactor located downstream of the catalyst layer (C) or the catalyst layer (D). The reaction gas is cooled to separate liquid in the reaction gas, forming a separated gas and a separated liquid. The oil-water separation of the reaction liquid yields an oil component from which at least a portion of water has been removed. At least a portion of the separated gas and at least a portion of the oil component are supplied to the adiabatic reactor as circulating gas and circulating liquid.

In the method for producing cumene according to the present invention (the first embodiment), the circulating gas and the circulating liquid, together with the raw materials, benzene, acetone, and hydrogen, are supplied to the adiabatic reactor.

In the present invention, the reaction liquid and reaction gas containing cumene collected from the outlet of the adiabatic reactor located downstream of the catalyst layer (C) or the catalyst layer (D) is separated into a reaction liquid and a reaction gas with a gas-liquid separator located downstream of the outlet of the adiabatic reactor. The gas-liquid separator is not particularly limited and may be a vertical drum. The cooling of the reaction gas for the separation into a separated gas and a separated liquid is generally performed with a gas-liquid separator. The gas-liquid separator is not particularly limited and may be a vertical drum. The oil-water separation of the reaction liquid yields an oil component from which at least a portion of water has been removed. A separator for the oil-water separation is not particularly limited and may be a horizontal drum having a lower boot or a horizontal drum having an internal partition. In addition to the reaction liquid, the separated liquid may also be supplied to the oil-water separator to perform oil-water separation.

In the present invention, before the separation of the reaction gas into a separated gas and a separated liquid and before the oil-water separation of the reaction liquid, the reaction gas and the reaction liquid are preferably cooled by heat exchange with a heat exchanger. The heat exchanger for use in heat exchange is not particularly limited and may be of any type that can perform heat exchange, for example, a spiral heat exchanger, a plate heat exchanger, a double-pipe heat exchanger, a shell and tube heat exchanger, a multi-tube heat exchanger, a spiral tube heat exchanger, a spiral plate heat exchanger, a tank coil heat exchanger, a tank jacket heat exchanger, or a direct contact liquid-liquid heat exchanger.

Since the reaction is an exothermic reaction, effective utilization of generated heat is effective from an energy-saving and economic point of view. Heat of reaction is generally recovered as steam by passing the reaction gas and the reaction liquid through a heat exchanger.

In the method for producing cumene according to the present invention (the first embodiment), at least a portion of the oil component is supplied to the adiabatic reactor as circulating liquid. Generally 5% to 100% by weight, preferably 30% to 100% by weight, of the oil component is supplied to the adiabatic reactor as circulating liquid.

The method for producing cumene according to the present invention (the second embodiment) preferably includes the steps (V') to (VII') as well as the steps (I') to (IV'). In the method for producing cumene according to the present invention (the second embodiment) including the steps (V') to (VII'), a portion of the oil component formed in the step (VI') is supplied to the adiabatic reactor for the step (I') as circulating liquid. In this case, generally 5% to 99% by weight, preferably 30% to 99% by weight, of the oil component formed in the step (VI') is supplied to the adiabatic reactor for the step (I') as circulating liquid.

The circulating liquid (oil component) contains various components, for example, benzene, acetone, isopropanol, diisopropyl ether, propylene, and cumene.

In the method for producing cumene according to the present invention (the first embodiment), at least a portion of the separated gas is supplied to the adiabatic reactor as circulating gas. Generally 9% to 100% by weight, preferably 30% to 100% by weight, of the separated gas is supplied to the adiabatic reactor as circulating gas.

The method for producing cumene according to the present invention (the second embodiment) preferably includes the steps (V') to (VII') as well as the steps (I') to (IV'). In the method for producing cumene according to the present invention (the second embodiment) including the steps (V') to (VII'), a portion of the separated gas formed in the step (V') is supplied to the adiabatic reactor for the step (I') as circulating gas. In this case, generally 9% to 100% by weight, preferably 30% to 100% by weight, of the separated gas formed in the step (V') is supplied to the adiabatic reactor for the step (I') as circulating gas.

In the method for producing cumene according to the present invention (the first embodiment), a portion of the oil component not returned to the adiabatic reactor is generally purified to produce cumene. Purification is performed by a known method, such as distillation. When the portion of the oil component not returned to the adiabatic reactor is purified by distillation, the purification may be performed with two distillation columns, for example, as illustrated in the flow chart of FIG. 2. In this case, light components having lower boiling points than cumene, such as benzene, are removed in the first distillation column, and heavy components having higher boiling points than cumene, such as diisopropylbenzene, are removed in the second distillation column. Thus, purified cumene can be produced. The light components removed in the first distillation column contain raw materials and reaction intermediates, such as benzene, acetone, and propylene. Thus, the light components are preferably returned to the adiabatic reactor as a portion of the raw materials used in the present invention.

In the method for producing cumene according to the present invention (the second embodiment), the reaction liquid and reaction gas containing cumene produced in the step (IV') is generally purified to produce cumene. Purification is performed by a known method, such as distillation. When the portion of the oil component not returned to the adiabatic reactor is purified by distillation, the purification may be performed, for example, with two distillation columns. In this case, light components having lower boiling points than cumene, such as benzene, are removed in the first distillation column, and heavy components having higher boiling points than cumene, such as diisopropylbenzene, are removed in the second distillation column. Thus, purified cumene can be produced. The light components removed in the first distillation column contain raw materials and reaction intermediates, such as benzene, acetone, and propylene. Thus, the light components are preferably returned to the adiabatic reactor for the step (I') as a portion of the raw materials used in the present invention.

The reaction liquid and reaction gas containing cumene produced in the step (IV') may be directly purified by distillation or, before being supplied to the distillation columns, may be cooled, subjected to gas-liquid separation, or subjected to oil-water separation. In the method for producing cumene according to the present invention (the second embodiment), the oil component is formed in the steps (V') to (VII'), and a portion of the oil component not returned to the adiabatic reactor for the step (I') is preferably supplied to the distillation columns for purification.

Figure 3:
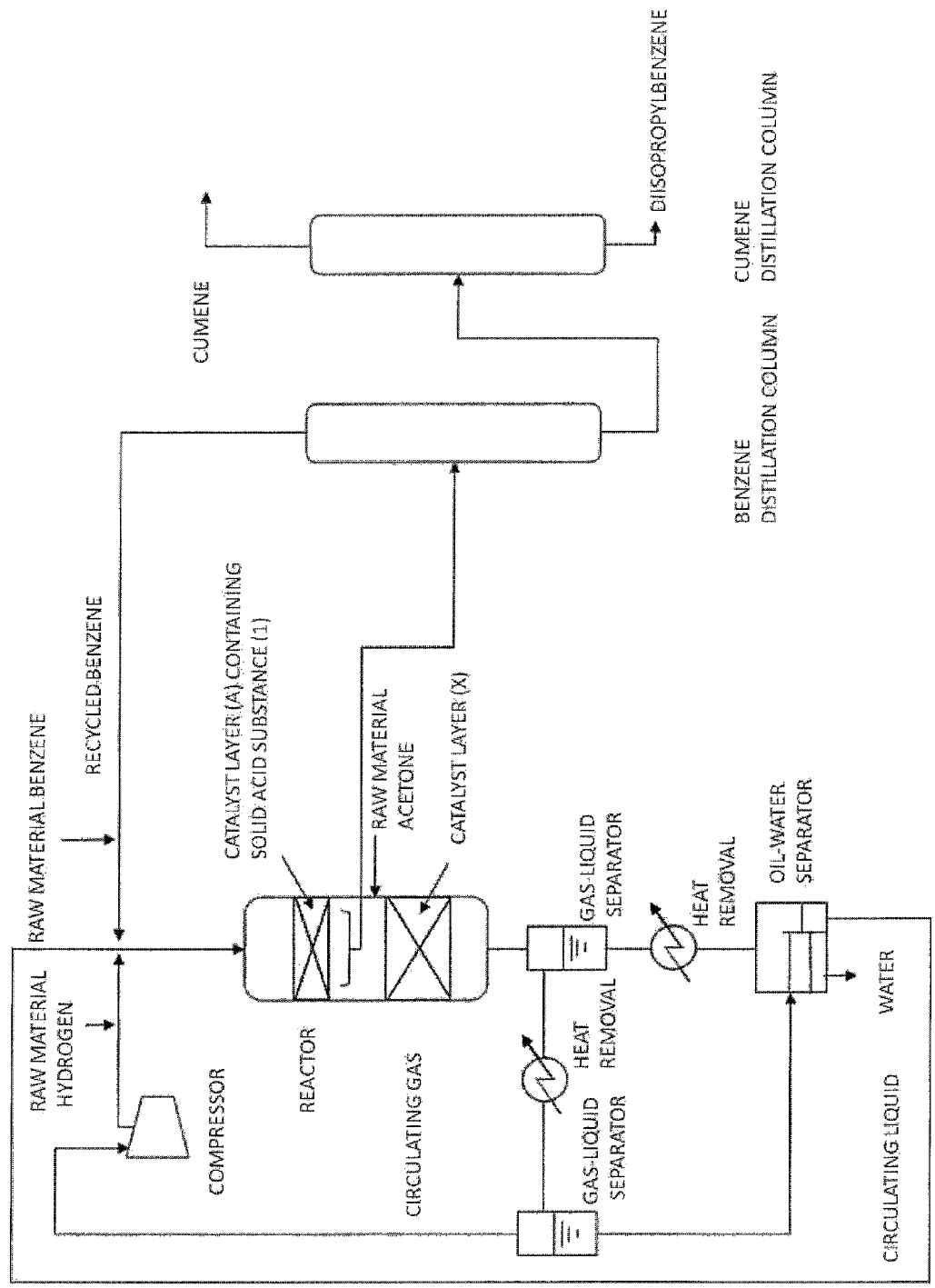
FIG. 3 is a flow chart of a method for producing cumene according to the present invention including the steps (I) to (V) (the first embodiment).

Preferably, the method for producing cumene according to the present invention (the first embodiment) further includes a step (V) of collecting reaction liquid and reaction gas containing cumene from an outlet of the adiabatic reactor located downstream of the catalyst layer (A) and upstream of the catalyst layer (B) or the catalyst layer (D) (see, for example, FIG. 3). In an adiabatic reactor used in the present invention, the installation of an outlet downstream of the catalyst layer (A) and upstream of the catalyst layer (B) or the catalyst layer (D) is preferred because it allows the collection of reaction liquid and reaction gas having a higher cumene concentration than reaction liquid and reaction gas containing cumene collected from an outlet of the adiabatic reactor located downstream of the catalyst layer (C) or the catalyst layer (D).

The reaction liquid and reaction gas containing cumene collected in the step (V) may be directly purified by distillation or, before being supplied to distillation columns, may be cooled, subjected to gas-liquid separation, or subjected to oil-water separation.

In the step (V), acetone is preferably supplied downstream of the outlet of the adiabatic reactor located downstream of the catalyst layer (A) and upstream of the catalyst layer (B) or the catalyst layer (D) in terms of the purification efficiency of cumene.

Figure 2:
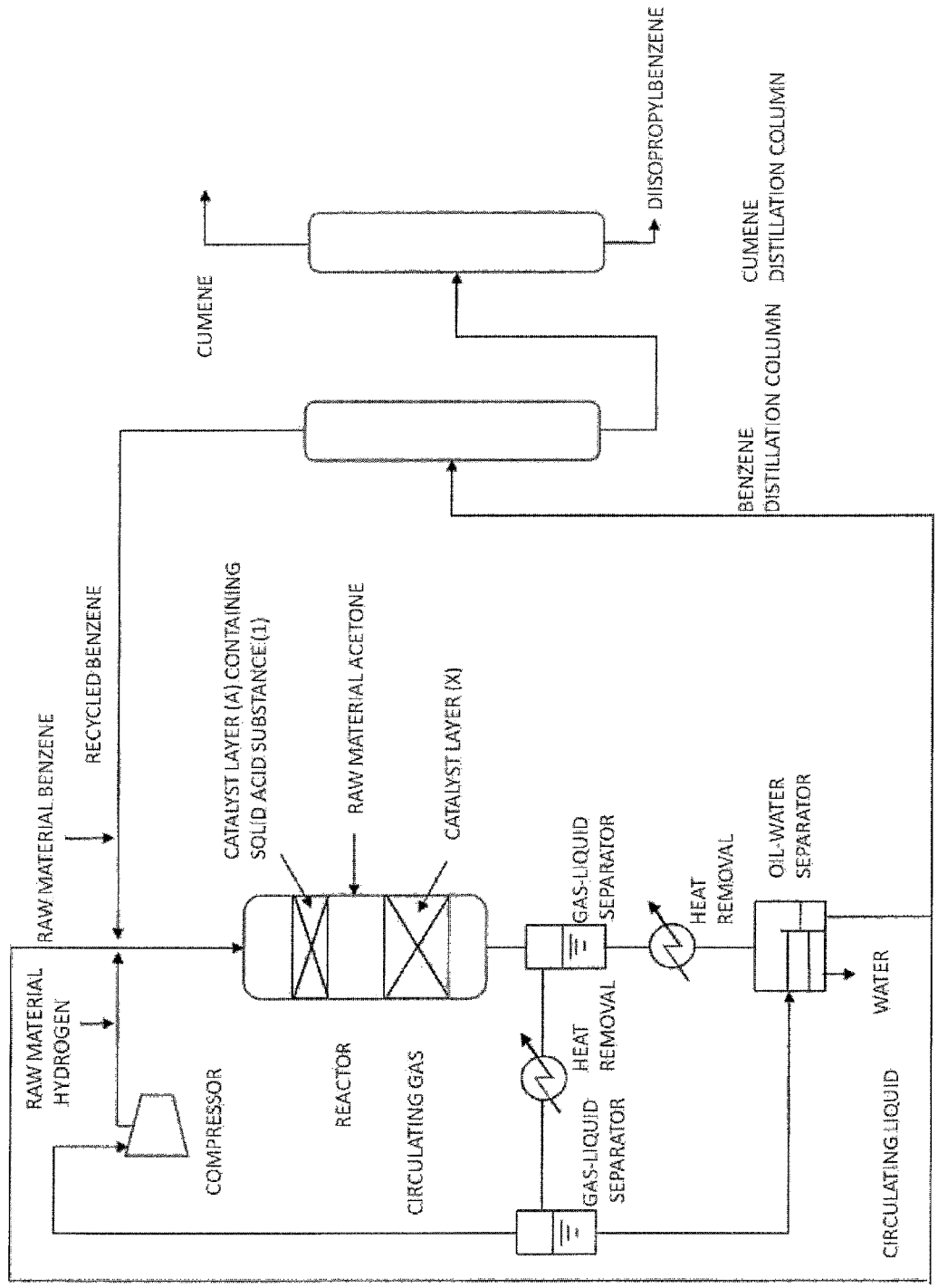
FIG. 2 is a flow chart of a method for producing cumene according to the present invention including the steps (I) to (IV) (a first embodiment).

FIGS. 2 and 3 are flow charts of a method for producing cumene according to an embodiment of the present invention (the first embodiment). FIG. 2 is a flow chart illustrating a method for producing cumene including the steps (I) to (IV) in which reaction liquid and reaction gas collected from an outlet of an adiabatic reactor located downstream of the catalyst layer (C) or the catalyst layer (D) are subjected to gas-liquid separation, cooling, and oil-water separation to yield an oil component, a portion of which is supplied to distillation columns to produce purified cumene. FIG. 3 illustrates a method for producing cumene including the steps (I) to (V) in which reaction liquid and reaction gas collected from an outlet of an adiabatic reactor located downstream of the catalyst layer (A) and upstream of the catalyst layer (B) or the catalyst layer (D) is purified to produce cumene. Reaction liquid and reaction gas collected from an outlet of the adiabatic reactor located downstream of the catalyst layer (C) or the catalyst layer (D) are supplied to the adiabatic reactor as circulating gas and circulating liquid through the steps (II), (III), and (IV).

Figure 4:
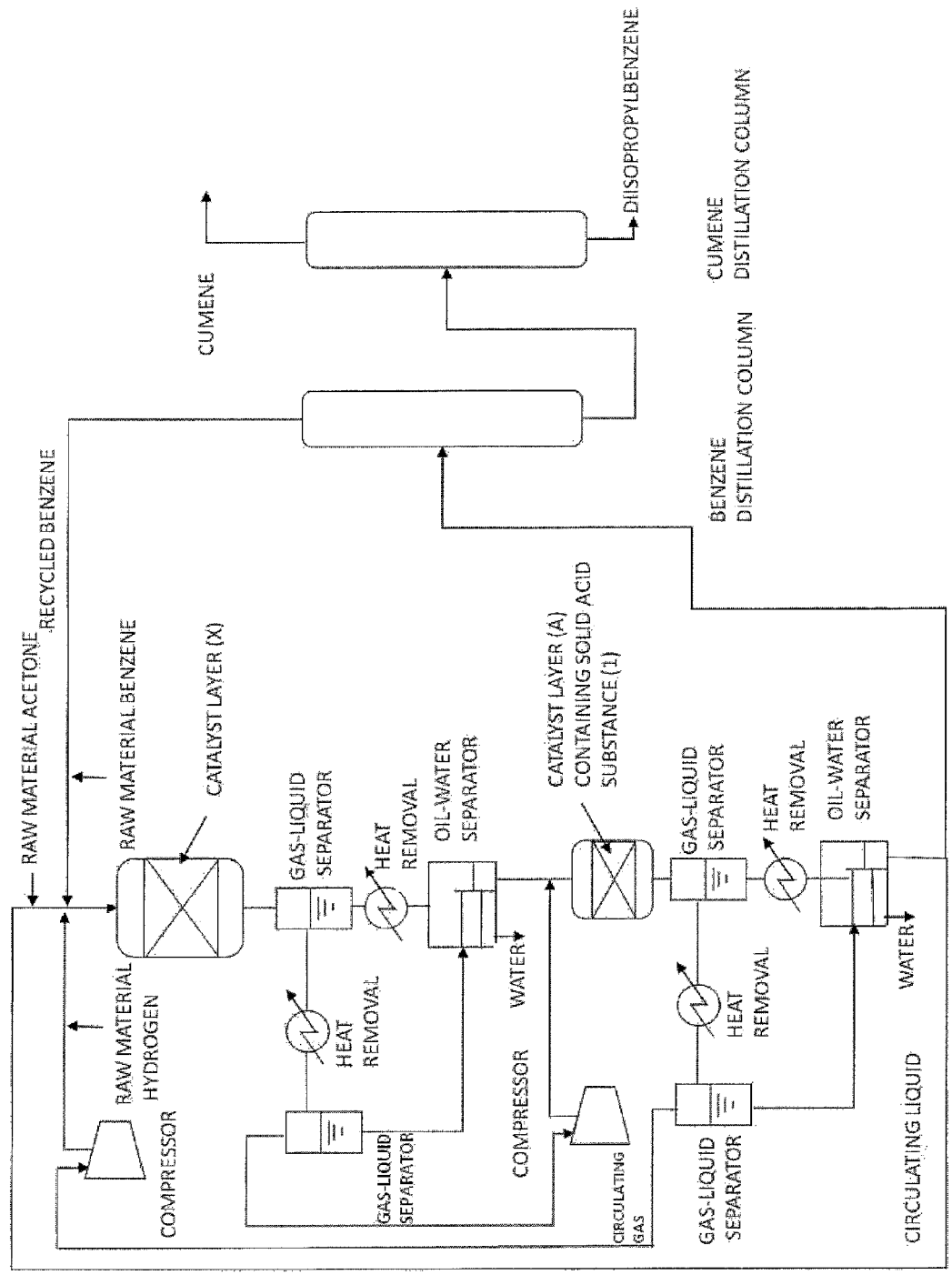
FIG. 4 is a flow chart of a method for producing cumene according to the present invention including the steps (I') to (VII') (a second embodiment).

FIG. 4 is a flow chart of a method for producing cumene according to an embodiment of the present invention (the second embodiment). FIG. 4 illustrates a method for producing cumene including the steps (I') to (IV') and the steps (V') to (VII') in which reaction liquid and reaction gas collected from an outlet of an adiabatic reactor located downstream of the catalyst layer (C) or the catalyst layer (D) are subjected to gas-liquid separation, cooling, and oil-water separation to yield an oil component, which is supplied to a catalyst layer (A) of a downstream adiabatic reactor. A portion of the oil component formed from the reaction liquid and reaction gas collected from the outlet of the adiabatic reactor through gas-liquid separation, cooling, and oil-water separation is supplied to distillation columns to produce purified cumene.

Catalyst layers (X) in FIGS. 2 to 4 denote two catalyst layers of the catalyst layer (B) and the catalyst layer (C) or denote the catalyst layer (D).

A method for producing phenol according to the present invention is characterized in that it includes the following steps (a) to (e), and the step (c) is performed in accordance with the method for producing cumene:

the step (a) of converting cumene into cumene hydroperoxide by oxidation;

the step (b) of converting cumene hydroperoxide into phenol and acetone by acidolysis;

the step (c) of synthesizing cumene by the reaction of benzene, acetone, and hydrogen using the acetone produced in the step (b);

the step (d) of purifying the cumene produced in the step (c); and the step (e) of supplying the cumene purified in the step (d) to the step (a).

In accordance with a method for producing phenol according to the present invention, acetone produced as a by-product associated with the production of phenol in the step (b) can be used in the step (c) to produce cumene.

In accordance with a method for producing phenol according to the present invention, phenol is produced from cumene in the steps (a) and (b), cumene is produced in the step (c) using acetone produced as a by-product, and in the step (e) cumene produced in the step (c) is supplied to the step (a). Theoretically, it is not necessary to supply acetone from outside the reaction system. Thus, this method is cost-effective. In an actual plant, it is difficult to recover 100% of the acetone, and acetone in an amount at least corresponding to the acetone lost is supplied to the reaction system.

A method for producing phenol according to the present invention may be variously modified without problems.

EXAMPLES

Although the present invention will be further described in the following examples, the present invention is not limited to these examples.

Comparative Example 1

A downflow pressurized liquid phase flow reaction was performed with a fixed-bed reaction apparatus equipped with a high-pressure feed pump, a high-pressure hydrogen mass flow, an electric furnace, a reactor having a catalyst-filled portion, and a back-pressure valve.

A SUS316 reactor having an inner diameter of 1 cm was charged with 2.0 g of a copper-zinc catalyst (manufactured by Sud-Chemie AG, product name ShiftMax 210, element mass %: Cu 32% to 35%, Zn 35% to 40%, and Al 6% to 7%) powder (classified into 250 to 500μ) as an upstream catalyst layer (a catalyst layer formed of metal components). After being plugged with quartz wool, the reactor was charged with 1.0 g of MCM-22 zeolite (prepared by compression molding at 20 MPa of a catalyst prepared in accordance with VERIFIED SYNTHESES OF ZEOLITIC MATERIALS Second Revised Edition 2001, P225 and classification into 250 to 500μ) as a downstream catalyst layer (a catalyst layer formed of a solid acid substance).

After the reactor was pressurized to 3 MPa with hydrogen, a liquid mixture of benzene/acetone/cumene (4.8/1/3.8 mole) and hydrogen gas in an amount of four times the number of moles of acetone were fed at a raw material feed rate of 25.0 g/h at 190° C. from a reactor inlet.

A product was sampled at a reactor outlet, and the amount of product was determined by GC analysis. Table 1 shows the experimental results.

Table 1 shows the experimental results at different raw material feed rates.

The WHSV (zeolite) had to be reduced to 0.9 to reduce the percentage of residual propylene to 0.1% or less. Because of equilibrium between acetone and isopropanol, the acetone conversion was no more than approximately 98%.

The WHSV was determined by dividing the raw material feed weight per hour by the weight (3 g) of the zeolite and the copper-zinc catalyst (see the following formula). The WHSV (zeolite) was determined by dividing the raw material feed weight per hour by the zeolite weight (1 g) (see the following formula). The raw material feed weight is the total weight of a liquid mixture of benzene/acetone/cumene (4.8/1/3.8 mole) and hydrogen fed to the reactor.

WHSV=Raw material feed weight per hour/(Copper-zinc catalyst weight+Zeolite weight)

WHSV(zeolite)=Raw material feed weight per hour/Zeolite weight

TABLE 1

| WHSV ($h^{-1}$) | WHSV($h^{-1}$) (zeolite) | Raw material feed rate (g/h) | Hydrogen (ml/min) | Water (wt %) | AC conversion | Selectivity for products (%)/AC | | | | | |
|---|---|---|---|---|---|---|---|---|---|---|---|
| | | | | | | IPA | IPE | Propylene | Cumene | DIPB | TIPB | Others |
| 0.3 | 0.9 | 0.9 | 1.5 | 2.0 | 98.2 | 0.0 | 0.0 | 0.1 | 55.8 | 42.1 | 0.8 | 1.2 |
| 0.9 | 2.7 | 2.7 | 4.1 | 2.0 | 98.1 | 0.0 | 0.0 | 0.9 | 55.0 | 42.3 | 0.8 | 1.0 |
| 1.6 | 4.7 | 4.7 | 7.3 | 2.0 | 98.1 | 0.3 | 0.0 | 8.6 | 48.2 | 41.2 | 0.5 | 1.2 |
| 4.5 | 13.6 | 13.6 | 21.2 | 2.0 | 98.2 | 1.2 | 0.5 | 32.6 | 39.1 | 24.8 | 0.5 | 1.3 |
| 6.0 | 18.1 | 18.1 | 27.8 | 1.9 | 98.0 | 1.5 | 0.5 | 39.5 | 28.7 | 28.2 | 0.4 | 1.2 |
| 8.4 | 25.2 | 25.2 | 38.6 | 1.9 | 98.5 | 3.0 | 0.6 | 53.4 | 22.0 | 19.7 | 0.3 | 1.0 |

AC = Acetone
IPA = Isopropanol
IPE = Diisopropyl ether
DIPB = Diisopropylbenzenes
TIPB = Triisopropylbenzenes An experiment (Example 1) was performed in which a solid acid substance was brought into contact with a model composition (IPA/IPE/propylene/cumene/p-DIPB(p-diisopropylbenzene)/1,3,5-TIPB(1,3,5-triisopropylbenzene) (molar ratio based on acetone)=1.5/0.5/39.5/28.7/28.2/0.4) corresponding to a composition which is a product at a WHSV (zeolite)=18.1 in Comparative Example 1 from which water has been removed. This experiment showed the extent to which the removal of water reduced the amount of catalyst required to complete the alkylation reaction (production of cumene) as compared with Comparative Example 1.

Example 1

A downflow pressurized liquid phase flow reaction was performed with a fixed-bed reaction apparatus equipped with a high-pressure feed pump, a high-pressure hydrogen mass flow, an electric furnace, a reactor having a catalyst-filled portion, and a back-pressure valve.

A SUS316 reactor having an inner diameter of 1 cm was charged with 1.0 g of MCM-22 zeolite (prepared by compression molding at 20 MPa of a catalyst prepared in accordance with VERIFIED SYNTHESES OF ZEOLITIC MATERIALS Second Revised Edition 2001, P225 and classification into 250 to 500μ) as a catalyst layer formed of a solid acid substance.

The reactor was pressurized to 3 MPa with hydrogen and was set at 165° C. Propylene and a composition not including propylene (composition: IPA/IPE/cumene/p-DIPB/1,3,5-TIPB (molar ratio based on acetone)=1.5/0.5/28.7/28.2/0.4) were supplied with two pumps. The ratio of propylene to the composition supplied was controlled with two pumps to meet the model composition (composition: IPA/IPE/propylene/cumene/p-DIPB/1,3,5-TIPB (molar ratio based on acetone) =1.5/0.5/39.5/28.7/28.2/0.4).

Propylene and the composition were fed at various feed rates (WHSVs). Hydrogen was fed at three quarters of the amount of hydrogen gas fed at the same WHSV (zeolite) as in Comparative Example 1.

A reaction product was sampled at a reactor outlet, and the amount of reaction product was determined by GC analysis. Table 2 shows the results. Removal of water produced dramatically improved the catalytic activity, and propylene disappeared at a WHSV of 8.2. The WHSV (zeolite-3) was 5.6 as determined from the total amount of zeolite catalyst taking account of the amount of zeolite used in the initial reaction (Comparative Example 1). This shows that propylene could disappear at a WHSV higher than the WHSV (zeolite) of 0.9 at which propylene was reduced to 0.1% in Comparative Example 1.

Thus, it was found that once water produced was removed, even when the temperature was reduced to 165° C., the alkylation reaction could be completed with a small amount of zeolite catalyst.

The WHSV was determined by dividing the raw material feed weight per hour by the zeolite weight (1 g) (see the following formula). The raw material feed weight is the total weight of the model composition and hydrogen fed to the reactor. The WHSV (zeolite-3) was determined by dividing the raw material feed weight per hour by the raw material feed rate divided by 18.1 and the zeolite weight used in Example 1 (see the following formula). The WHSV (including a hydrogenation catalyst) is the reduced value of the total amount of catalysts taking account of the amount of copper-zinc catalyst and zeolite used in the initial reaction (Comparative Example 1) and was determined by dividing by the raw material feed rate divided by 6.0 and the zeolite weight used in Example 1.

WHSV=Raw material feed weight per hour/Zeolite weight

WHSV(zeolite-3)=Raw material feed weight per hour/ (Raw material feed rate/18.1+Zeolite weight)

WHSV(including hydrogenation catalyst)=Raw material feed weight per hour/(Raw material feed rate/ 6.0+Zeolite weight)

Comparative Example 2

A downflow pressurized liquid phase flow reaction was performed with a fixed-bed reaction apparatus equipped with a high-pressure feed pump, a high-pressure hydrogen mass flow, an electric furnace, a reactor having a catalyst-filled portion, and a back-pressure valve.

A SUS316 reactor having an inner diameter of 1 cm was charged with 2.0 g of a copper-zinc catalyst (manufactured by Sud-Chemie AG, product name ShiftMax 210, element mass %: Cu 32% to 35%, Zn 35% to 40%, and Al 6% to 7%) powder (classified into 250 to 500μ) as an upstream catalyst layer (a catalyst layer formed of metal components). After being plugged with quartz wool, the reactor was charged with 1.0 g of β-zeolite (manufactured by Catalysts & Chemicals Industries Co., Ltd., prepared by compression molding at 20 MPa and classification into 250 to 500μ) as a downstream catalyst layer (a catalyst layer formed of a solid acid substance).

After the reactor was pressurized to 3 MPa with hydrogen, a liquid mixture of benzene/acetone/cumene (4.8/1/3.8 mole) and hydrogen gas in an amount of four times the number of moles of acetone were fed at a raw material feed rate of 25.0 g/h at 190° C. from a reactor inlet.

A product was sampled at a reactor outlet, and the amount of product was determined by GC analysis. Table 3 shows the experimental results.

Table 3 shows the experimental results at different raw material feed rates.

The WHSV (zeolite) had to be reduced to 1.0 to reduce the percentage of residual propylene to 0.1% or less. Because of equilibrium between acetone and isopropanol, the acetone conversion was no more than approximately 98%.

The WHSV was determined by dividing the raw material feed weight per hour by the weight (3 g) of the zeolite and the copper-zinc catalyst (see the following formula). The WHSV (zeolite) was determined by dividing the raw material feed weight per hour by the zeolite weight (1 g) (see the following formula). The raw material feed weight is the total weight of a liquid mixture of benzene/acetone/cumene (4.8/1/3.8 mole) and hydrogen fed to the reactor.

TABLE 2

| WHSV ($h^{-1}$) | WHSV($h^{-1}$) (zeolite-3) | WHSV($h^{-1}$) (including hydrogenation catalyst) | Hydrogen (ml/min) | Molar concentration (%) | | | | | | | |
|---|---|---|---|---|---|---|---|---|---|---|---|
| | | | | AC | IPA | IPE | Propylene | Cumene | DIPB | TIPB | Others |
| 4.3 | 3.5 | 2.5 | 5.2 | 0.5% | 0.0% | 0.0% | 0.0% | 96.9% | 2.4% | 0.0% | 0.0% |
| 6.1 | 4.6 | 3.0 | 7.3 | 0.4% | 0.0% | 0.0% | 0.0% | 97.0% | 2.5% | 0.1% | 0.1% |
| 8.2 | 5.6 | 3.5 | 9.8 | 0.4% | 0.0% | 0.0% | 0.0% | 97.0% | 2.5% | 0.0% | 0.0% |
| 14.7 | 8.1 | 4.3 | 17.6 | 0.4% | 0.0% | 0.0% | 0.3% | 96.9% | 2.4% | 0.1% | 0.0% |
| 20.1 | 9.5 | 4.6 | 24.1 | 0.4% | 0.0% | 0.0% | 0.4% | 96.9% | 2.2% | 0.0% | 0.0% |

AC = Acetone

IPA = Isopropanol

IPE = Diisopropyl ether

DIPB = Diisopropylbenzenes

TIPB = Triisopropylbenzenes

WHSV=Raw material feed weight per hour/(Copper-zinc catalyst weight+Zeolite weight)

WHSV(zeolite)=Raw material feed weight per hour/Zeolite weight

A reaction product was sampled at a reactor outlet, and the amount of reaction product was determined by GC analysis. Table 4 shows the results. Removal of water produced dramatically improved the catalytic activity, and propylene dis-

TABLE 3

| WHSV ($h^{-1}$) | WHSV($h^{-1}$) (zeolite) | Raw material feed rate (g/h) | Hydrogen (ml/min) | Water (wt %) | AC conversion | Selectivity for products (%)/AC | | | | | |
|---|---|---|---|---|---|---|---|---|---|---|---|
| | | | | | | IPA | IPE | Propylene | Cumene | DIPB | TIPB | Others |
| 0.3 | 1.0 | 1.0 | 1.6 | 2.0 | 97.8 | 0.0 | 0.0 | 0.0 | 30.4 | 67.2 | 1.0 | 1.4 |
| 0.9 | 2.7 | 2.7 | 4.3 | 2.0 | 98.1 | 0.0 | 0.0 | 0.5 | 30.6 | 66.8 | 0.8 | 1.3 |
| 1.5 | 4.5 | 4.5 | 7.2 | 2.0 | 98.0 | 0.2 | 0.0 | 6.6 | 27.2 | 64.4 | 0.6 | 1.0 |
| 4.5 | 13.6 | 13.6 | 21.8 | 2.0 | 98.0 | 1.1 | 0.8 | 32.0 | 21.0 | 43.5 | 0.6 | 1.0 |
| 6.7 | 20.2 | 20.2 | 32.3 | 1.9 | 98.0 | 1.5 | 1.2 | 38.5 | 20.0 | 37.5 | 0.4 | 0.9 |
| 8.4 | 25.2 | 25.2 | 40.3 | 1.9 | 98.0 | 2.8 | 1.0 | 50.5 | 15.5 | 29.0 | 0.3 | 0.9 |

AC = Acetone
IPA = Isopropanol
IPE = Diisopropyl ether
DIPB = Diisopropylbenzenes
TIPB = Triisopropylbenzenes An experiment (Example 2) was performed in which a solid acid substance was brought into contact with a model composition (IPA/IPE/propylene/cumene/p-DIPB/1,3,5-TIPB (molar ratio based on acetone)=1.5/1.2/38.5/20.0/37.5/0.4) corresponding to a composition which is a product at a WHSV (zeolite)=20.2 in Comparative Example 2 from which water has been removed. This experiment showed the extent to which the removal of water reduced the amount of catalyst required to complete the alkylation reaction (production of cumene) as compared with Comparative Example 2.

Example 2

A downflow pressurized liquid phase flow reaction was performed with a fixed-bed reaction apparatus equipped with a high-pressure feed pump, a high-pressure hydrogen mass flow, an electric furnace, a reactor having a catalyst-filled portion, and a back-pressure valve.

A SUS316 reactor having an inner diameter of 1 cm was charged with 1.0 g of β-zeolite (manufactured by Catalysts & Chemicals Industries Co., Ltd., prepared by compression molding at 20 MPa and classification into 250 to 500μ) as a catalyst layer formed of a solid acid substance.

The reactor was pressurized to 3 MPa with hydrogen and was set at 155° C. Propylene and a composition not including propylene (composition: IPA/IPE/cumene/p-DIPB/1,3,5-TIPB (molar ratio based on acetone)=1.5/1.2/20.0/37.5/0.4) were supplied with two pumps. The ratio of propylene to the composition supplied was controlled with two pumps to meet the model composition (composition: IPA/IPE/propylene/cumene/p-DIPB/1,3,5-TIPB (molar ratio based on acetone)=1.5/1.2/38.5/20.0/37.5/0.4).

Propylene and the composition were fed at various feed rates (WHSVs). Hydrogen was fed at three quarters of the amount of hydrogen gas fed at the same WHSV (zeolite) as in Comparative Example 2.

appeared at a WHSV of 8.5. The WHSV (zeolite-3) was 6.0 as determined from the total amount of zeolite catalyst taking account of the amount of zeolite used in the initial reaction (Comparative Example 2). This shows that propylene could disappear at a WHSV higher than the WHSV of 1.0 at which propylene was reduced to 0.0% in Comparative Example 2.

Thus, it was found that once water produced was removed, even when the temperature was reduced to 155° C., the alkylation reaction could be completed with a small amount of zeolite catalyst.

The WHSV was determined by dividing the raw material feed weight per hour by the zeolite weight (1 g) (see the following formula). The raw material feed weight is the total weight of the model composition and hydrogen fed to the reactor. The WHSV (zeolite-3) was determined by dividing the raw material feed weight per hour by the raw material feed rate divided by 20.2 and the zeolite weight used in Example 2 (see the following formula). The WHSV (including a hydrogenation catalyst) is the reduced value of the total amount of catalysts taking account of the amount of copper-zinc catalyst and zeolite used in the initial reaction (Comparative Example 2) and was determined by dividing by the raw material feed rate divided by 6.7 and the zeolite weight used in Example 2.

WHSV=Raw material feed weight per hour/Zeolite weight

WHSV(zeolite-3)=Raw material feed weight per hour/(Raw material feed rate/20.2+Zeolite weight)

WHSV(including hydrogenation catalyst)=Raw material feed weight per hour/(Raw material feed rate/6.7+Zeolite weight)

TABLE 4

| WHSV ($h^{-1}$) | WHSV($h^{-1}$) (zeolite-3) | WHSV($h^{-1}$) (including hydrogenation catalyst) | Hydrogen (ml/min) | Molar concentration (%) | | | | | | | |
|---|---|---|---|---|---|---|---|---|---|---|---|
| | | | | AC | IPA | IPE | Propylene | Cumene | DIPB | TIPB | Others |
| 4.0 | 3.3 | 2.5 | 4.8 | 0.4% | 0.0% | 0.0% | 0.0% | 95.8% | 3.6% | 0.1% | 0.1% |
| 6.0 | 4.6 | 3.2 | 7.2 | 0.4% | 0.0% | 0.0% | 0.0% | 95.0% | 4.3% | 0.1% | 0.1% |

TABLE 4-continued

| WHSV (h⁻¹) | WHSV(h⁻¹) (zeolite-3) | WHSV(h⁻¹) (including hydrogenation catalyst) | Hydrogen (ml/min) | Molar concentration (%) | | | | | | | |
|---|---|---|---|---|---|---|---|---|---|---|---|
| | | | | AC | IPA | IPE | Propylene | Cumene | DIPB | TIPB | Others |
| 8.5 | 6.0 | 3.7 | 10.2 | 0.4% | 0.0% | 0.0% | 0.0% | 94.9% | 4.4% | 0.1% | 0.1% |
| 15.0 | 8.6 | 4.6 | 18.0 | 0.4% | 0.0% | 0.0% | 0.3% | 95.4% | 3.8% | 0.1% | 0.1% |
| 20.5 | 10.1 | 5.0 | 24.6 | 0.5% | 0.0% | 0.0% | 0.4% | 95.2% | 3.7% | 0.1% | 0.1% |

AC = Acetone
IPA = Isopropanol
IPE = Diisopropyl ether
DIPB = Diisopropylbenzenes
TIPB = Triisopropylbenzenes

The invention claimed is:

1. A method for producing an alkylated aromatic compound, comprising:
a step (i) of producing a reaction product (a1) containing the alkylated aromatic compound and water by the reaction of an aromatic compound, a ketone, and hydrogen using a metal component containing at least one metallic element selected from the group consisting of copper, nickel, cobalt, and rhenium and a solid acid substance;
a step (ii) of forming a dehydrated product (a2) from at least a portion of the reaction product (a1) by removing at least a portion of the water in the reaction product (a1); and
a step (iii) of producing a reaction product (a3) containing the alkylated aromatic compound by bringing at least a portion of the dehydrated product (a2) into contact with a solid acid substance.

2. The method for producing an alkylated aromatic compound according to claim 1, wherein the water content of the reaction product (a1) ranges from 0.5% to 10% by weight.

3. The method for producing an alkylated aromatic compound according to claim 1, wherein
the step (ii) includes
a step (ii-1) of forming a reaction gas and a reaction liquid by the gas-liquid separation of the reaction product (a1),
a step (ii-2) of forming a separated gas and a separated liquid by cooling the reaction gas to separate liquid in the reaction gas, and
a step (ii-3) of forming an oil component from which at least a portion of water has been removed by oil-water separation of the reaction liquid,
wherein the separated gas and the oil component are used as at least a portion of the dehydrated product (a2).

4. The method for producing an alkylated aromatic compound according to claim 3, wherein the step (ii-3) is a step of forming an oil component from which at least a portion of water has been removed by oil-water separation of the reaction liquid and the separated liquid formed in the step (ii-2).

5. The method for producing an alkylated aromatic compound according to claim 1, wherein the step (i) is performed in an adiabatic reactor.

6. The method for producing an alkylated aromatic compound according to claim 1, wherein the metal component further contains at least one element selected from the group consisting of group IIB elements, group IIIA elements, group VIB elements, and group VIII elements (except nickel and cobalt).

7. The method for producing an alkylated aromatic compound according to claim 1, wherein the solid acid substance is zeolite.

8. A method for producing cumene, wherein the aromatic compound and the ketone in the method for producing an alkylated aromatic according to claim 1 are benzene and acetone, respectively.

9. A method for producing cumene, comprising:
a step (I) of supplying benzene, acetone, and hydrogen to
an adiabatic reactor that includes, from the upstream side,
a catalyst layer (A) containing a solid acid substance (1),
a catalyst layer (B) containing a metal component containing at least one metallic element selected from the group consisting of copper, nickel, cobalt, and rhenium, and a catalyst layer (C) containing a solid acid substance (2), or
an adiabatic reactor that includes, from the upstream side, the catalyst layer (A) containing the solid acid substance (1) and a catalyst layer (D) containing a metal component containing at least one metallic element selected from the group consisting of copper, nickel, cobalt, and rhenium and the solid acid substance (2)
and collecting reaction liquid and reaction gas containing cumene from an outlet of the adiabatic reactor located downstream of the catalyst layer (C) or the catalyst layer (D);
a step (II) of forming a separated gas and a separated liquid by cooling the reaction gas to separate liquid in the reaction gas;
a step (III) of forming an oil component from which at least a portion of water has been removed by oil-water separation of the reaction liquid; and
a step (IV) of supplying at least a portion of the separated gas and at least a portion of the oil component to the adiabatic reactor as circulating gas and circulating liquid.

10. The method for producing cumene according to claim 9, further comprising a step (V) of collecting reaction liquid and reaction gas containing cumene from an outlet of the adiabatic reactor located downstream of the catalyst layer (A) and upstream of the catalyst layer (B) or the catalyst layer (D).

11. A method for producing cumene, comprising:
a step (I') of supplying benzene, acetone, and hydrogen to
an adiabatic reactor that includes, from the upstream side,
a catalyst layer (B) containing a metal component containing at least one metallic element selected from the group consisting of copper, nickel, cobalt, and rhenium and a catalyst layer (C) containing a solid acid substance (2), or
an adiabatic reactor that includes a catalyst layer (D) containing a metal component containing at least one metallic element selected from the group consisting of copper, nickel, cobalt, and rhenium and the solid acid substance (2)

and collecting reaction liquid and reaction gas containing cumene from an outlet of the adiabatic reactor located downstream of the catalyst layer (C) or the catalyst layer (D);

a step (II') of forming a separated gas and a separated liquid by cooling the reaction gas to separate liquid in the reaction gas;

a step (III') of forming an oil component from which at least a portion of water has been removed by oil-water separation of the reaction liquid; and a step (IV') of supplying at least a portion of the separated gas and at least a portion of the oil component to an adiabatic reactor that includes a catalyst layer (A) containing a solid acid substance (1) and producing reaction liquid and reaction gas containing cumene.

12. The method for producing cumene according to claim 11, further comprising:

a step (V') of forming a separated gas and a separated liquid by cooling the reaction gas produced in the step (IV') to separate liquid in the reaction gas;

a step (VI') of forming an oil component from which at least a portion of water has been removed by oil-water separation of the reaction liquid produced in the step (IV'); and a step (VII') of supplying at least a portion of the separated gas and a portion of the oil component to the adiabatic reactor used in the step (I') as circulating gas and circulating liquid.

13. The method for producing cumene according to claim 9, wherein the metal component further contains at least one element selected from the group consisting of group IIB elements, group IIIA elements, group VIB elements, and group VIII elements (except nickel and cobalt).

14. The method for producing cumene according to claim 9, wherein at least one of the solid acid substance (1) and the solid acid substance (2) is zeolite.

15. The method for producing cumene according to claim 14, wherein the zeolite is zeolite having a 10, 11, or 12-membered ring structure.

16. The method for producing cumene according to claim 14, wherein the zeolite is at least one zeolite selected from the group consisting of beta zeolite and MCM-22.

17. A method for producing phenol, comprising the following steps (a) to (e), wherein the step (c) is performed in accordance with a method for producing cumene according to claim 8:

the step (a) of converting cumene into cumene hydroperoxide by oxidation;

the step (b) of converting cumene hydroperoxide into phenol and acetone by acidolysis;

the step (c) of synthesizing cumene by the reaction of benzene, acetone, and hydrogen using the acetone produced in the step (b);

the step (d) of purifying the cumene produced in the step (c); and the step (e) of supplying the cumene purified in the step (d) to the step (a).

* * * * *